United States Patent
Chin et al.

(10) Patent No.: US 8,622,912 B2
(45) Date of Patent: Jan. 7, 2014

(54) TRANSCRANIAL DOPPLER APPARATUS

(75) Inventors: Robert C. Chin, Austin, TX (US); Sridhar Madala, Houston, TX (US); Graham Patrick Sattler, Houston, TX (US)

(73) Assignee: Fabrico Technology, Inc., Austin, TX (US)

( * ) Notice: Subject to any disclaimer, the term of this patent is extended or adjusted under 35 U.S.C. 154(b) by 154 days.

(21) Appl. No.: 13/182,185

(22) Filed: Jul. 13, 2011

(65) Prior Publication Data

US 2012/0022377 A1    Jan. 26, 2012

Related U.S. Application Data

(60) Provisional application No. 61/363,762, filed on Jul. 13, 2010.

(51) Int. Cl.
*A61B 8/00* (2006.01)

(52) U.S. Cl.
USPC .......................................................... 600/453

(58) Field of Classification Search
None
See application file for complete search history.

(56) References Cited

U.S. PATENT DOCUMENTS

| | | | |
|---|---|---|---|
| 4,517,985 A * | 5/1985 | Teslawski et al. ............ 600/446 |
| 4,817,621 A | 4/1989 | Aaslid |
| 5,058,592 A | 10/1991 | Whisler |
| 5,070,880 A | 12/1991 | Gomez et al. |
| 5,630,416 A * | 5/1997 | Uchikura et al. ............ 600/444 |
| 5,844,140 A | 12/1998 | Seale |
| 6,196,972 B1 | 3/2001 | Moehring |
| 6,213,945 B1 | 4/2001 | Tynan |
| 6,328,694 B1 | 12/2001 | Michaeli |
| 6,344,024 B1 | 2/2002 | Brucher et al. |
| 6,468,219 B1 * | 10/2002 | Njemanze ..................... 600/454 |
| 6,524,249 B2 | 2/2003 | Moehring et al. |
| 6,547,736 B1 | 4/2003 | Moehring et al. |
| 6,547,737 B2 | 4/2003 | Njeemanze |
| 6,616,611 B1 | 9/2003 | Moehring |
| 6,682,483 B1 | 1/2004 | Abend et al. |
| 6,682,488 B2 | 1/2004 | Abend |
| 6,702,743 B2 | 3/2004 | Michaeli |
| 2002/0103436 A1 | 8/2002 | Njemanze |
| 2002/0151790 A1 | 10/2002 | Abend |
| 2003/0013956 A1 | 1/2003 | Michaeli |
| 2003/0060711 A1 | 3/2003 | Michaeli |
| 2003/0225335 A1 | 12/2003 | Njemanze |
| 2004/0002654 A1 | 1/2004 | Davidson et al. |
| 2004/0138563 A1 | 7/2004 | Moehring et al. |
| 2004/0158155 A1 | 8/2004 | Njemanze |
| 2004/0210135 A1 | 10/2004 | Hynynen et al. |
| 2004/0267127 A1 | 12/2004 | Abend et al. |
| 2005/0004461 A1 | 1/2005 | Abend |
| 2005/0033174 A1 | 2/2005 | Moehring et al. |
| 2005/0075568 A1 | 4/2005 | Moehring |
| 2005/0124897 A1 | 6/2005 | Chopra |
| 2005/0251041 A1 | 11/2005 | Moehring |
| 2006/0079773 A1 | 4/2006 | Mourad et al. |
| 2007/0016046 A1 | 1/2007 | Mozayeni et al. |
| 2007/0016050 A1 | 1/2007 | Moehring et al. |
| 2007/0165881 A1 | 7/2007 | Ramakrishnan et al. |
| 2007/0293760 A1 | 12/2007 | Schaafsma |

* cited by examiner

Primary Examiner — Long V. Le
Assistant Examiner — Bo J Peng
(74) Attorney, Agent, or Firm — Larson Newman, LLP (57) ABSTRACT

The disclosure is directed to a transcranial Doppler probe. The transcranial Doppler probe includes a spherical bearing, a piezoelectric transducer pivotally attached to the spherical bearing, and first and second rods coupled to the piezoelectric transducer. The first rod is configured to pivot the piezoelectric transducer around a first pivot axis and the second rod is configured to pivot the piezoelectric transducer around a second pivot axis.

20 Claims, 8 Drawing Sheets

TRANSCRANIAL DOPPLER APPARATUS

CROSS-REFERENCE TO CORRESPONDING APPLICATION(S)

The present application is a non-provisional of U.S. Provisional Patent Application No. 61/363,762, entitled "TRANSCRANIAL DOPPLER PROBE" filed on Jul. 13, 2010, the entirety of which is herein incorporated by reference.

GOVERNMENT LICENSE RIGHTS

The U.S. Government has a paid-up license in this invention and the right in limited circumstances to require the patent owner to license others on reasonable terms as provided for by the terms of Contract No. NNJ06HI36C awarded by the National Aeronautics and Space Administration.

FIELD OF THE DISCLOSURE

This disclosure generally relates to transcranial Doppler probes.

BACKGROUND

The blood that flows through the brain distributes nutrients to the brain and removes wastes. This flow maintains the high rate of metabolism necessary for the brain to function. Restrictions in blood flow may occur from vessel narrowing (stenosis), clot formation (thrombosis), blockage (embolism), or blood vessel rupture (hemorrhage). Lack of sufficient blood flow (ischemia) threatens brain tissue and may cause a stroke.

The flow of blood through the arteries in the brain can be analyzed using transcranial Doppler ultrasonography (TCD). Blood flow velocity is recorded by emitting an acoustic wave from the ultrasound probe, which then is reflected by various materials. The TCD probe measures the reflected acoustic wave. The direction and the speed of blood flow relative to the TCD probe can be measured by determining the phase shift of acoustic wave reflected from objects in the blood, such as red blood cells. For example, red blood cells moving away from the probe cause the frequency to decrease and faster moving red blood cells cause a greater change in the frequency. Combined with other tests, this information can be used to locate restrictions in the blood vessels in the brain, and to track changes in blood flow over time. In this way, TCD gives valuable information about the site of a stroke and the patient's progress after a stroke. TCD is also used to evaluate the contraction of blood vessels that can occur if a blood vessel ruptures.

SUMMARY

In a particular embodiment, the disclosure is directed to a transcranial Doppler probe including a spherical bearing, a piezoelectric transducer, and first and second rods. The piezoelectric transducer is pivotally attached to the spherical bearing and the first and second rods are coupled to the piezoelectric transducer. The first rod is configured to pivot the piezoelectric transducer around a first pivot axis and the second rod is configured to pivot the piezoelectric transducer around a second pivot axis.

In another embodiment, the disclosure is directed to a transcranial Doppler probe including a piezoelectric transducer and first and second motors. The first motor is coupled to the piezoelectric transducer and is configured to pivot the piezoelectric transducer around a first pivot axis. The second motor is coupled to the piezoelectric transducer and is configured to pivot the piezoelectric transducer around a second pivot axis. The first and second motors are arranged in parallel and second axis is perpendicular to the first axis.

In a further embodiment, the disclosure is directed to a method of transcranial Doppler probe including a spherical bearing and a piezoelectric transducer pivotally attached to the spherical bearing. The transcranial Doppler probe further includes first and second rods coupled to the piezoelectric transducer and first and second motors. The first motor is coupled to the first rod and is configured to cause movement of the first rod to pivot the piezoelectric transducer around a first pivot axis. The second motor is coupled to the second rod and is configured to cause movement of the second rod to pivot the piezoelectric transducer around a second pivot axis. The first and second motors are arranged in parallel and second axis is perpendicular to the first axis.

In an additional embodiment, the disclosure is directed to a transcranial Doppler system including a processing component and a transcranial Doppler probe in communication with the processing component. The transcranial Doppler probe includes a spherical bearing, a piezoelectric transducer, and first and second rods. The piezoelectric transducer is pivotally attached to the spherical bearing. The first and second rods are coupled to the piezoelectric transducer. The first rod is configured to pivot the piezoelectric transducer around a first pivot axis and the second rod is configured to pivot the piezoelectric transducer around a second pivot axis.

In a further embodiment, the disclosure is directed to a transcranial Doppler system including a processing component and a transcranial Doppler probe in communication with the processing component. The transcranial Doppler probe includes a piezoelectric transducer and first and second motors coupled to the piezoelectric transducer. The first motor is configured to pivot the piezoelectric transducer around a first pivot axis and the second motor is configured to pivot the piezoelectric transducer around a second pivot axis. The first and second motors are arranged in parallel and second axis is perpendicular to the first axis.

In another embodiment, the disclosure is directed to a method of diagnosing a patient including placing a transcranial Doppler probe on a head of the patient and generating acoustic pulses directed into the head of the patient. The transcranial Doppler probe includes a spherical bearing, a piezoelectric transducer, and first and second rods. The piezoelectric transducer is pivotally attached to the spherical bearing, and the first and second rods are coupled to the piezoelectric transducer. The first rod is configured to pivot the piezoelectric transducer around a first pivot axis and the second rod is configured to pivot the piezoelectric transducer around a second pivot axis. The method further includes receiving reflections of the acoustic pulses caused by structures within the head of the patient, processing the reflections, and identifying a circulatory anomaly within the head of the patient.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION

In a particular embodiment, a transcranial Doppler probe includes a piezoelectric transducer coupled to a spherical bearing to rotate about at least two axes. The rotation may be driven by rods, each coupled to a motor. In an example, the motors are arranged in parallel.

FIGS. 1 through 6 illustrate an exemplary embodiment of a transcranial Doppler (TCD) probe 100. The TCD probe 100 can include a mounting platform 102. A mounting rod 104 having a proximal end 106 and a distal end 108 can be attached to the mounting platform 102 at the distal end 108. The proximal end 106 of the mounting rod 104 can be attached to a spherical bearing 110 through a central hole 112. The spherical bearing 110 may have a spherical or frustospherical shape characterized by a convex outer surface that permits rotation about at least two axes. An outer ring 114 of the spherical bearing 110 can pivot around a central portion 116. The outer ring 114 can be attached to a mounting cup 118 shown in FIG. 3. A piezoelectric transducer 120 can be mounted on the mounting cup 118.

In a particular example, the probe may have length in the range of 40 mm to 100 mm, such as a range of 50 mm to 80 mm, or even a range of 60 mm to 75 mm. The probe may have a width in a range of 20 mm to 50 mm, such as a range of 25 mm to 45 mm, or even a range of 30 mm to 40 mm. The probe may have a height in a range of 10 mm to 30 mm, such as a range of 10 mm to 25 mm, or even a range of 15 mm to 20 mm. The length, width and height are orthogonal dimensions, wherein the height is parallel to the general direction of transmissions from the piezoelectric transducer 120 and the length and width are perpendicular to the general direction of transmissions.

Figure 1:
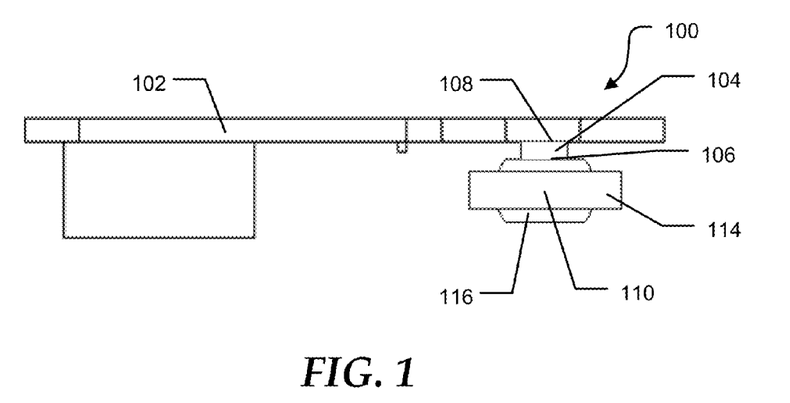
FIGS. 1 through 6 include diagrams depicting an exemplary transcranial Doppler probe.
Figure 2:
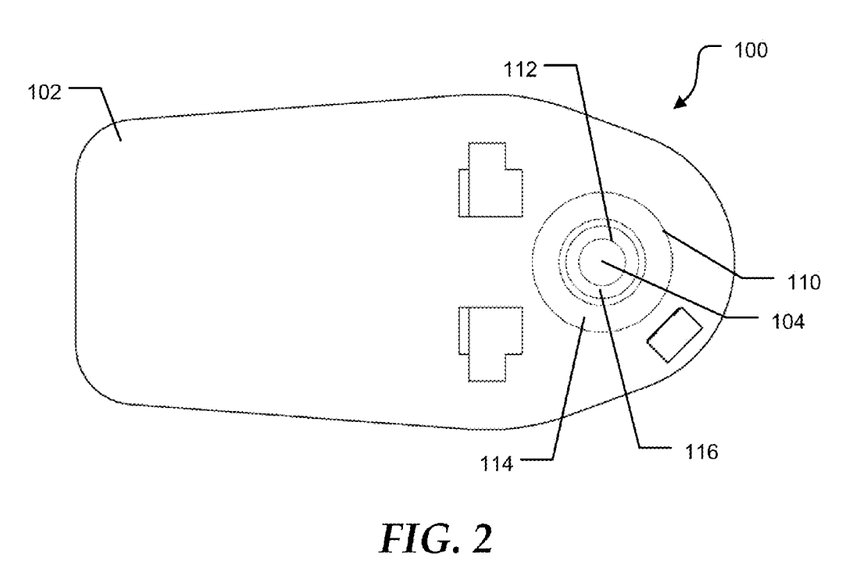
Figure 3:
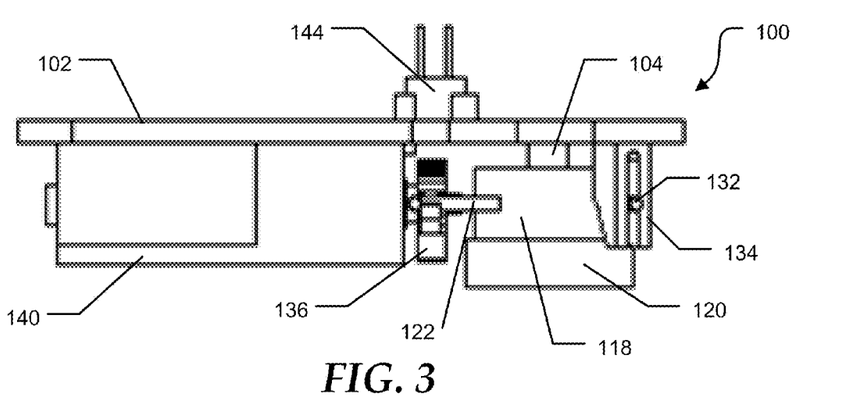
Figure 4:
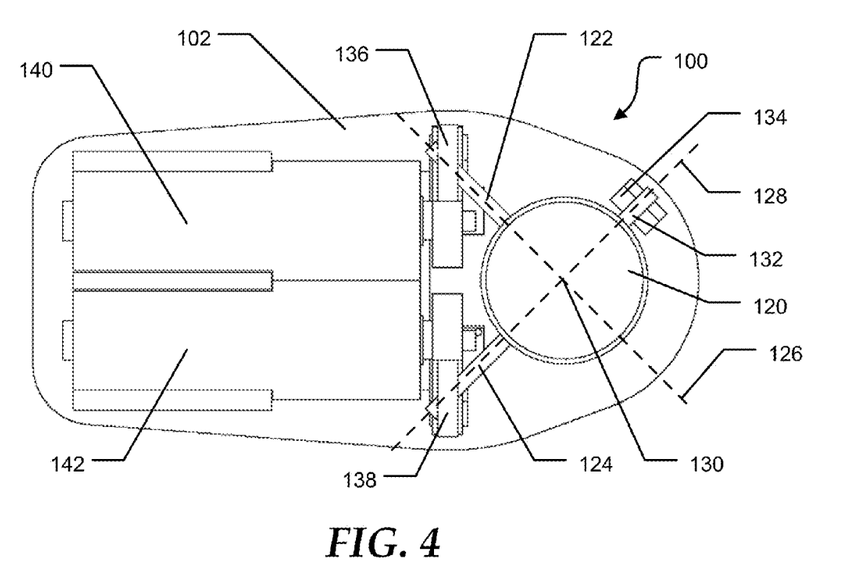

As shown in FIG. 4, control arms 122 and 124 can extend radially from the mounting cup 118 at about 90° angles. The axes 126 and 128 of the control arms 122 and 124 extend through a central pivot point 130 of the spherical bearing 110. Additionally, a guide pin 132 can be coupled to the mounting cup 118 (shown in FIG. 3) and may be coaxial with control arm 124. The guide pin 132 can fit in a guide pin slide 134 and substantially limit the rotation of the mounting cup 118 within at least one plane while permitting rotation about at least two axes.

Figure 5:
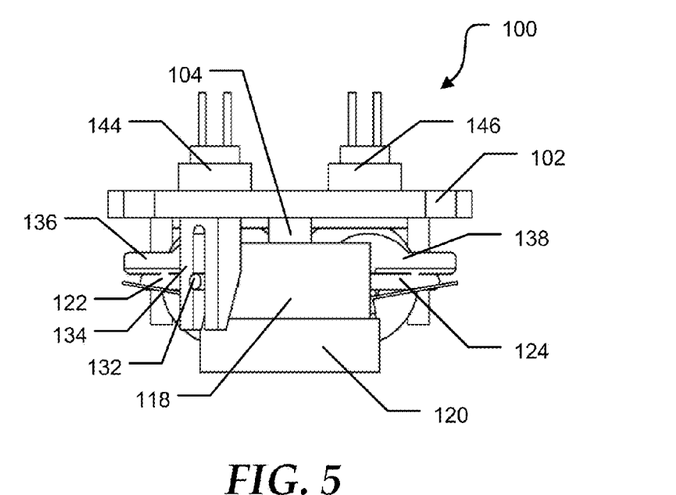

The control arms 122 and 124 can be coupled to drive levers 136 and 138 respectively. The drive levers 136 and 138 can be connected to motors 140 and 142. Motors 140 and 142 can be mounted in parallel on the mounting platform 102. Referring to FIG. 5, feedback sensors 144 and 146 can be mounted on the mounting platform 102 to monitor the position of the piezoelectric transducer 120.

The motors 140 and 142 can cause the rotation of drive levers 136 and 138, respectively. The drive levers 136 and 138 can torque the control arms 122 and 124 and cause the mounting cup 118 to pivot about the central pivot 130 of the spherical bearing 110. The mounting cup 118 can simultaneously pivot around the axis 126 of control arm 122 and the axis 128 of control arm 124. The mounting cup 118 may have an angular movement (pivot range) of at least about 15° around the axis 126 of the control arm 122 or relative to a plane parallel to a horizontal plane of a housing of the transcranial Doppler probe, such as at least about 20°, preferably at least about 30°. Additionally, the mounting cup 118 may have an angular movement of at least about 15° around the axis 128 of the control arm 124 or relative to a plane parallel to a horizontal plane of a housing of the transcranial Doppler probe, such as at least about 20°, preferably at least about 30°. As such, the mounting cup 118 can pivot around the central pivot point 130 of the spherical bearing 110 in all directions. The mounting cup 118 may contact the mounting platform 102 at the extremes of the range of motion. Movement of the mounting cup 118 can allow an ultrasound beam produced by the piezoelectric transducer 120 to smoothly and continuously scan the interior volume of a cylindrical cone. Feedback sensors 144 and 146 can monitor the angular position of the ultrasound beam within the cylindrical cone and provide feedback for precise control of the motion of the piezoelectric transducer 120. In an embodiment, feedback sensors 144 and 146 can be IR sensors positioned to detect the rotational position of the drive levers 136 and 138.

Figure 6:
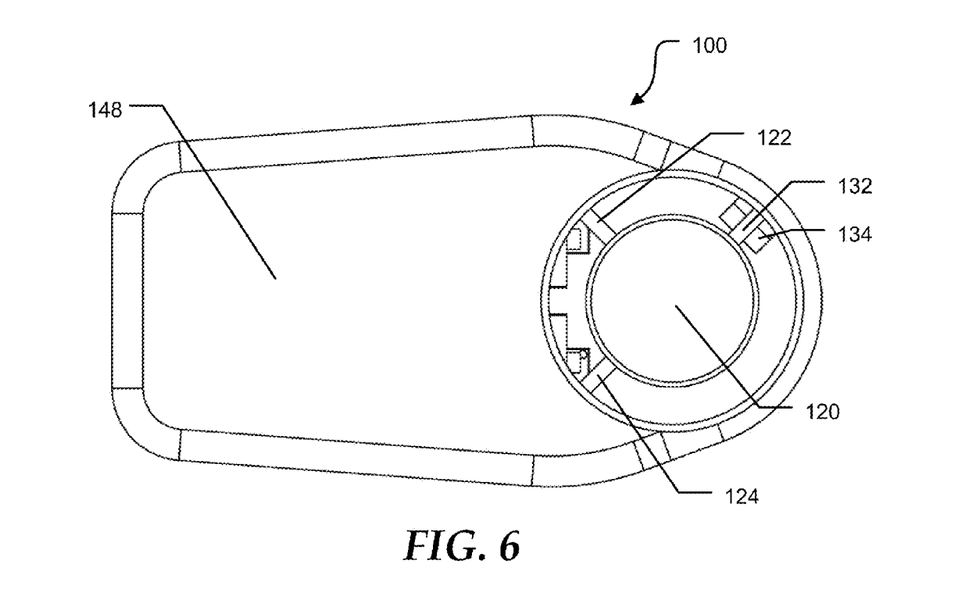

Referring to FIG. 6, a cover 148 can be attached to the mounting platform 102 and may substantially cover the components of the TCD probe 100. The cover 148 may have an opening 150 providing access between the piezoelectric transducer 120 and the patient.

Figure 7:
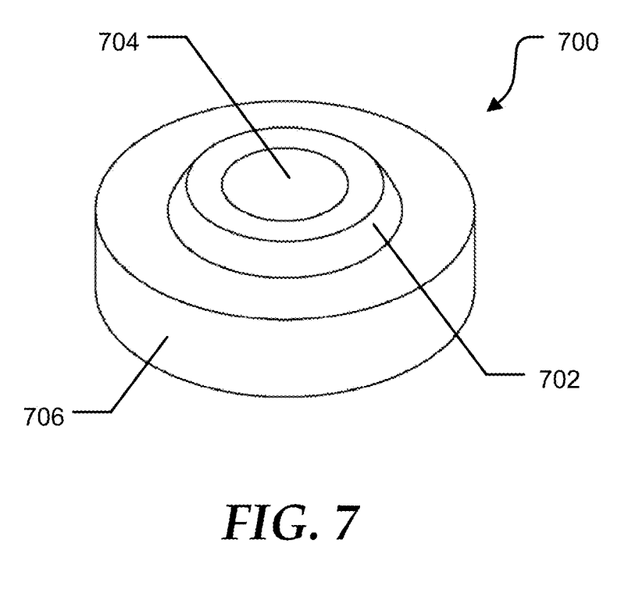
FIG. 7 includes a diagram depicting an exemplary spherical bearing.

FIG. 7 illustrates an exemplary spherical bearing 700, such as spherical bearing 110. The spherical bearing 700 can have a central portion 702 and a central hole 704 formed through the central portion 702. The central hole 704 can be configured for coupling to a mounting rod, such as mounting rod 104. Additionally, the spherical bearing 700 can have an outer ring 706 positioned around the central portion 702. The outer ring 706 can pivot around the central portion 702. In an embodiment, the spherical bearing 700 may be lubricated between the central portion 702 and the outer ring 706.

Figure 8:
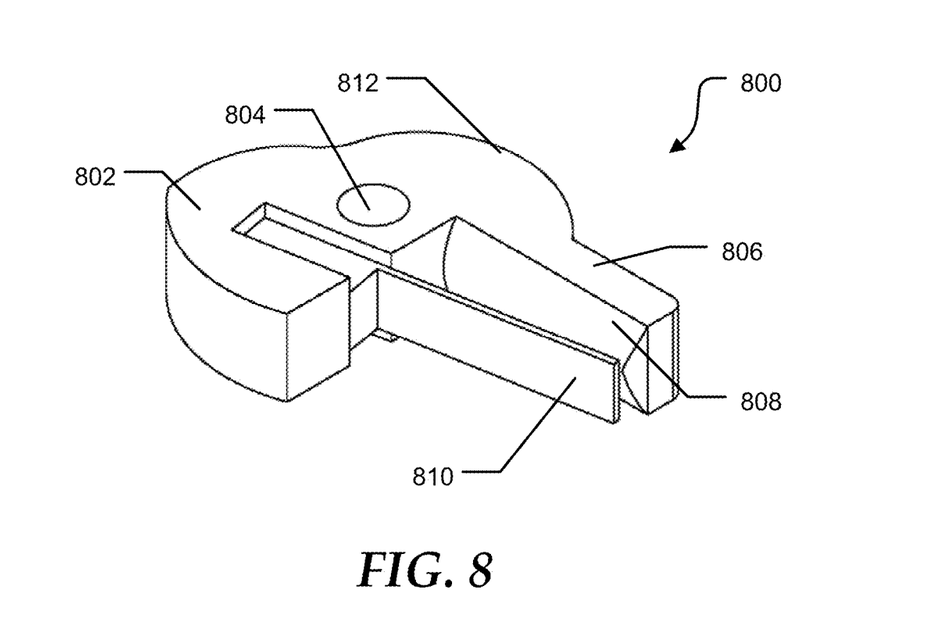
FIGS. 8 and 9 include diagrams depicting an exemplary drive lever.
Figure 9:
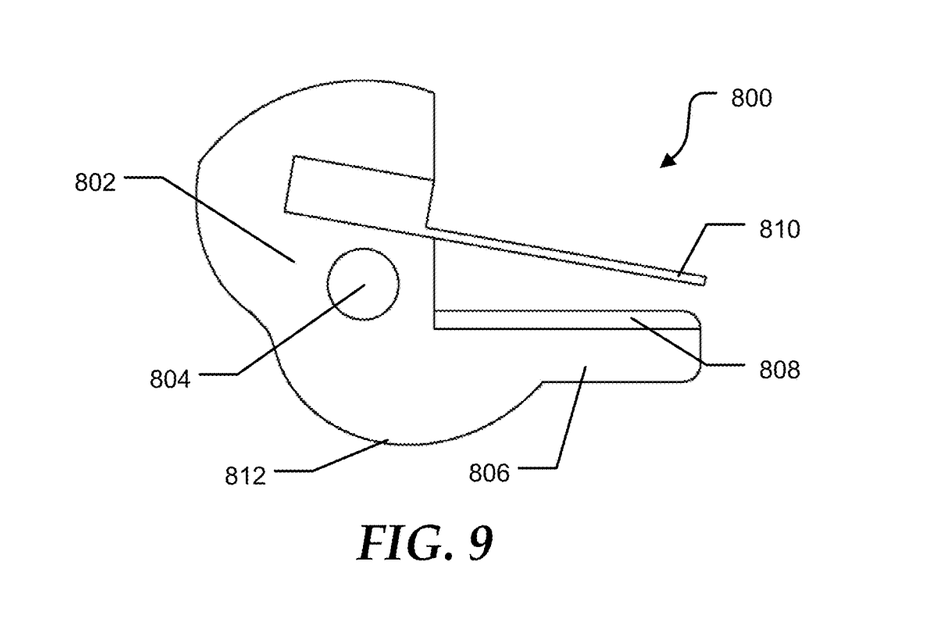

FIGS. 8 and 9 illustrate an exemplary drive lever or gear 800, such as drive levers 136 and 138, that torques a drive arm to pivot the piezoelectric transducer around an axis. In a particular example, the drive lever 800 has an axis of rotation that forms an angle in a range of 35° to 55° with the axis around with the transducer pivots, such as approximately 45°. The drive lever 800 can include a main portion 802 with a central hole 804 and a drive arm 806. The central hole 804 can be configured for attaching to a motor, such as motors 140 and 142. The drive arm 806 can include a curved drive surface 808, such as a convex drive surface to contract a control arm, such as control arms 122 and 124. The control arm may slide along the curved drive surface 808 as the drive lever 800 rotates. The drive lever 800 can further include a leaf spring 810 for holding the control arm in contact with the curved drive surface 808, such that the drive lever 800 maintains contact with the control arm when rotated in both a clockwise and counter clockwise direction. In an exemplary embodiment, the main portion 802 can include a cammed surface 812. The cammed surface 812 may provide feedback for a feedback sensor, such as feedback sensor 144 and 146. For example, the feedback sensor may measure the distance between the feedback sensor and the cammed surface 812. As the drive lever 800 is rotated, the distance between the motion sensor and the cammed surface 812 may vary, such that the rotational position of the drive lever 800 can be determined by measuring the distance between the motion sensor and the cammed surface 812.

Figure 10:
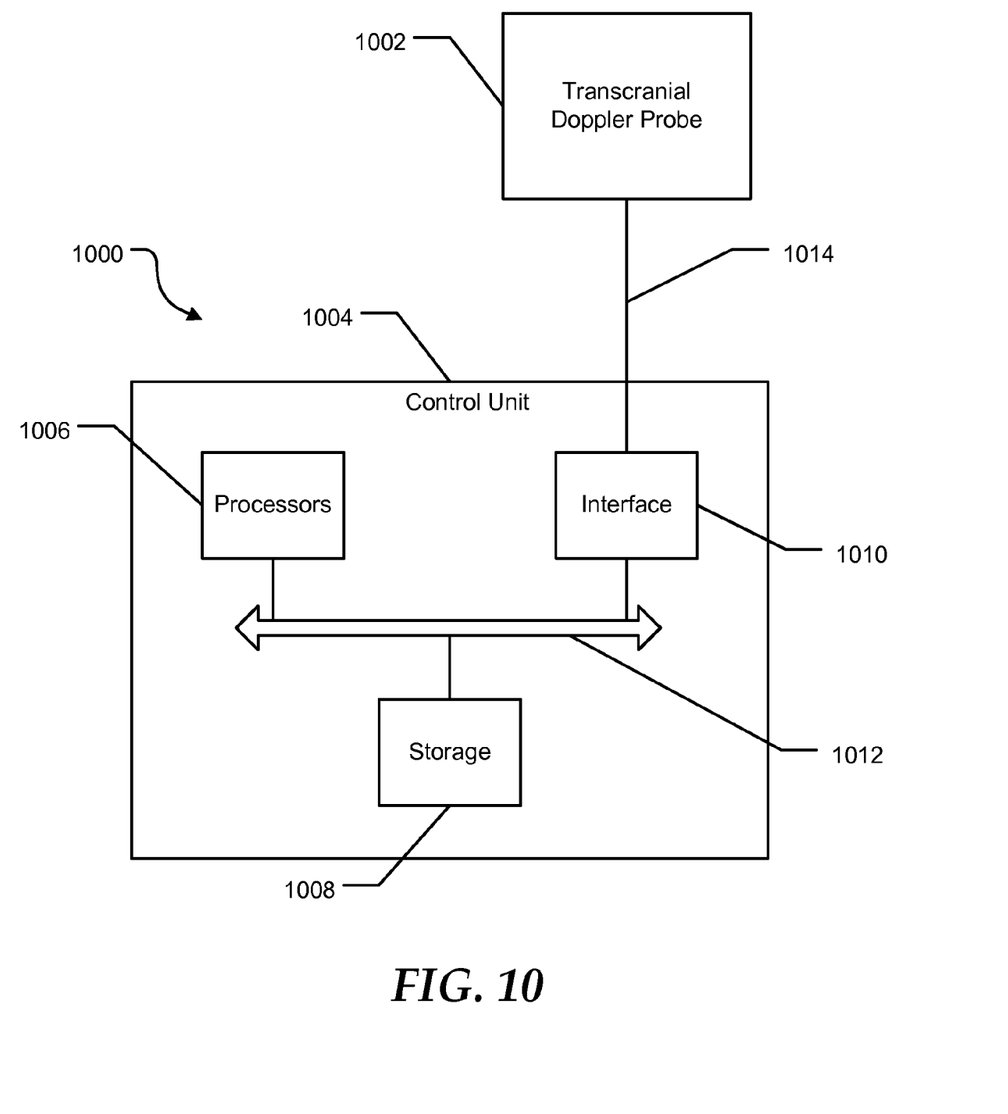
FIG. 10 includes a diagram depicting an exemplary transcranial Doppler system.

FIG. 10 illustrates an exemplary transcranial Doppler system 1000. The system can include a transcranial Doppler probe 1002 and a control unit 1004. The control unit 1004 can include one or more processors 1006, storage 1008, and an interface 1010. The processor 1006, storage 1008, and interface 1010 may be connected through a bus 1012. Alternatively, the storage 1008 may be connected to the processor 1006 separately from the interface 1010. The transcranial Doppler probe 1002 can communicate with the control unit 1004 through the interface 1010. In an embodiment, a cable 1014 can connect the transcranial Doppler probe 1002 with the interface 1010 of the control unit 1004. In an alternative embodiment, the communication between the transcranial Doppler probe 1002 and the control unit 1004 can be wireless. For example, the probe 1002 and the control unit 1004 may communicate using a wireless protocol, such as Bluetooth®. The processor 1006 can send instructions to and receive signals from the transcranial Doppler probe 1002 through the interface 1010. The instructions may include aiming instructions, such as for altering the tip/tilt angle of a piezoelectric transducer, or may include pulsing instructions to start, stop, or change the acoustic pulses produced by the piezoelectric transducer.

In an exemplary embodiment, the control unit 1004 may control the transcranial Doppler probe 1002 to emit a pulse transmission in the sonic range of 0.3 MHz to 100 MHz, such as a range of 0.5 MHz to 50 MHz, a range of 1 MHz to 25 MHz, a range of 1.5 MHz to 20 MHz, or even a range of 1.4 MHz to 5 MHz. In addition, the transcranial Doppler probe 1002 may be configured to receive echo signals at frequencies within the same range as the transmission. In an example, the control unit 1004 may perform Doppler or power Doppler quadrature demodulations of RF data at ranges of at least 3 times the transmission frequency, such as at least 4 times the transmission frequency. For example, when the transmission frequency is 2 MHz ultrasonic, data may be electronically collected at 8 MHz, and the data may be demodulated.

The processor 1004 may process the signals received from the transcranial Doppler probe 1002 and store the results in the storage 1008. Alternatively, the unprocessed signals from the transcranial Doppler probe 1002 can be stored in the storage 1008 for later retrieval and processing. In an example, the processor 1004 includes a digital signal processor, such as a processor having a clock speed of at least 500 MHz.

In a particular embodiment, the control unit 1004 may include a manual interface (not shown), such as a touch screen interface, keyboard, mouse, ball controller, or stick controller to permit manipulation of the direction the transcranial Doppler probe 1002 is projecting. Alternatively or in combination, the processor 1006 of the control unit 1004 may automatically manipulate the probe 1002. For example, a user may utilize the manual interface to provide a general direction to be explored and the processor 1006 may adjust the direction to improve a signal based on feedback from the probe 1002. Such automated control of the probe direction may be used for automatic emboli detection.

In another embodiment, the system 1000 may implement transtemporal window location. According to an exemplary method, the transtemporal area is scanned while transmitting and using a very short receive gate. Analyzing backscatter results in evaluation of bone thickness and density. Comparing the ultrasound wave scattered off of the bone from various locations permits determining which location experiences the least scattering. Such a technique can be combined with variable frequency ultrasound transmission. A signal may be provided through the control unit 1004 to indicate when the transcranial Doppler probe 1002 is located in a desirable position.

Figure 12:
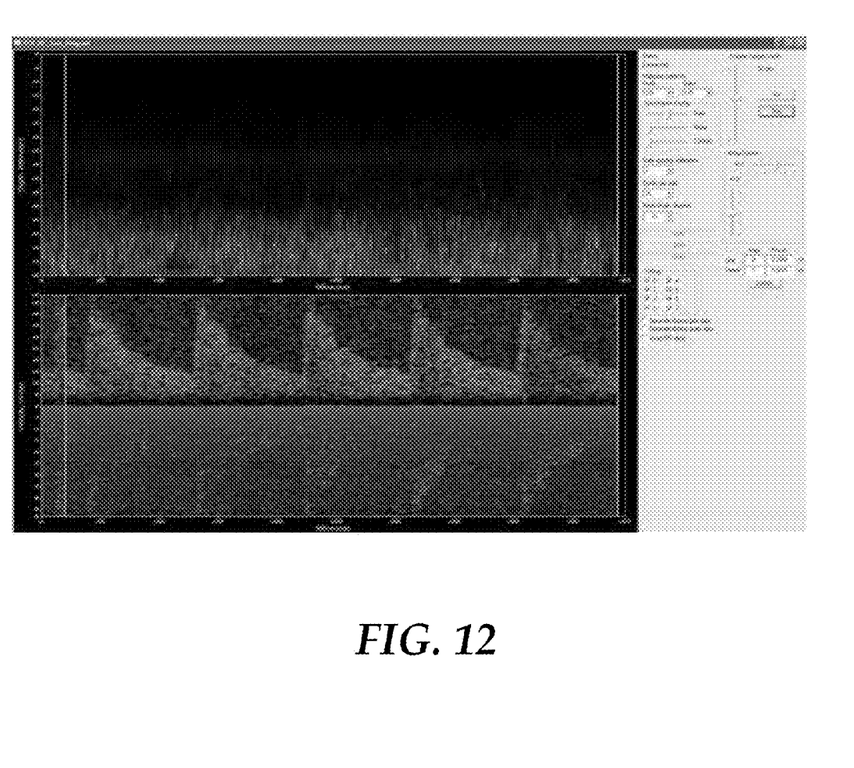
FIG. 12 includes an illustration of an exemplary display.

The control unit 1004 may also include additional interfaces (not illustrated) to permit input from other devices, such as pulse monitors, blood pressure measuring devices, respiratory measuring devices, and other medical devices. Data from such devices may be displayed in conjunction with the measured flow in cerebral vessels. For example, FIG. 12 includes an illustration of an exemplary display. In addition, data may be transmitted to another computation system for further analysis or storage. For example, a USB interface may provided to a personal computing device.

In a particular embodiment, the control unit 1004 may be implemented as a handheld device having a touch screen interface. In an example, the probe 1002 may communicate with the control unit 1004 through a USB interface. In another example, the interface 1010 includes a wireless interface to access the probe 1002, such as a Bluetooth® interface. The touch screen interface may provide control elements for manipulation of the direction the probe 1002 is projecting and measuring.

Figure 11:
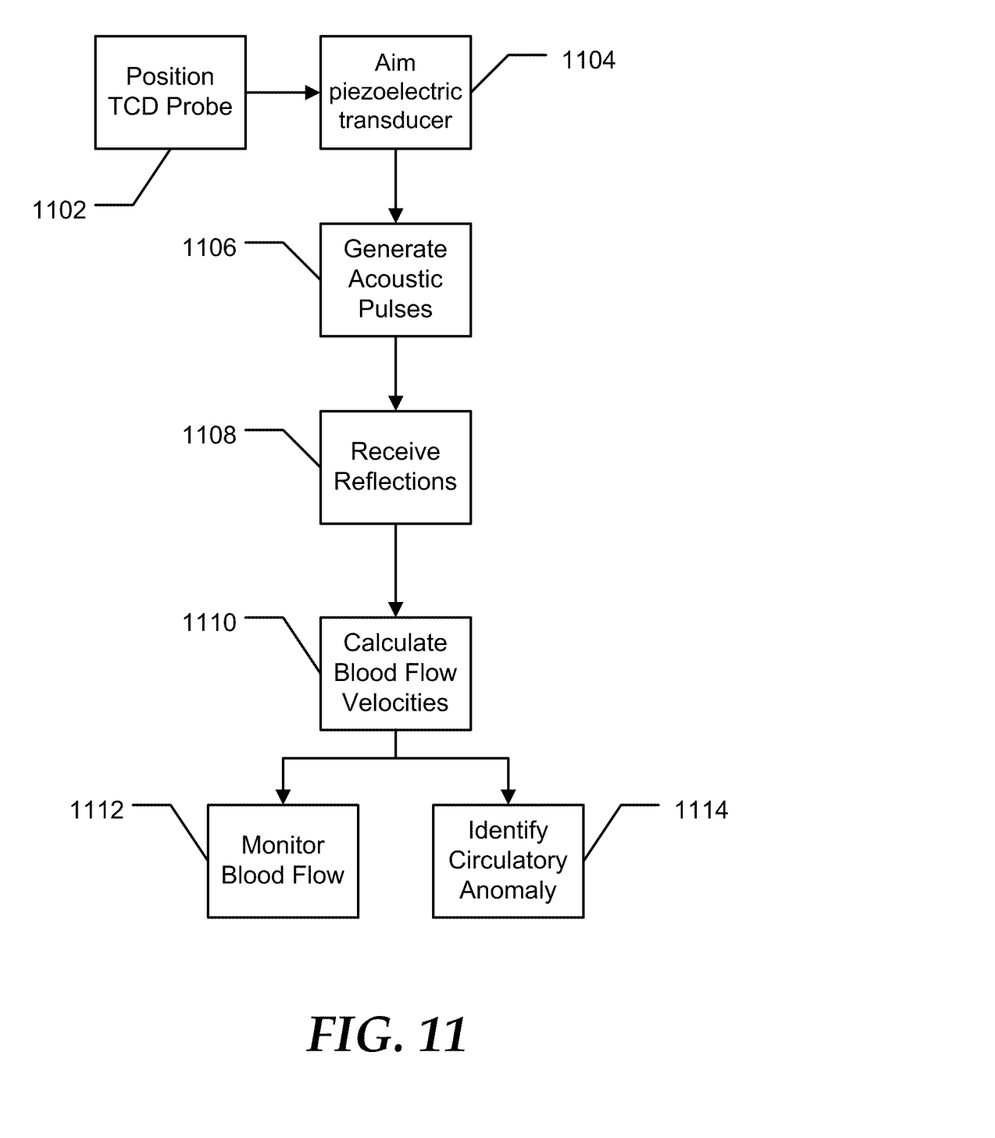
FIG. 11 includes a flow diagram depicting an exemplary method for use of a transcranial Doppler system.

FIG. 11 illustrates an exemplary method of using a transcranial Doppler system, such as transcranial Doppler system 500. As illustrated at 1102, the transcranial Doppler probe can be positioned on the head of the patient. For example, the transcranial Doppler probe may be placed near the temple of the patient.

As illustrated at 1104, the piezoelectric transducer can be aimed. The piezoelectric transducer may be aimed by adjusting the tip/tilt of the piezoelectric transducer to aim the acoustic pulses towards an area of interest, such as towards the blood vessels in the cranial cavity of the patient. In particular, a device connected to the probe can be used to adjust the orientation of the piezoelectric transducer. Once an orientation is configured, the transcranial Doppler probe can generate acoustic signals directed into the cranial cavity of the patient, as illustrated at 1106. The acoustic pulses travel into the tissues of the cranial cavity. Structures within the cavity cause reflections of the acoustic pulses. Specifically, objects traveling within blood vessels can reflect the acoustic pulses. The frequency of the reflected acoustic pulses is altered based on the velocity of the flow through the blood vessel.

As illustrated at 1108, the transcranial Doppler probe can receive the reflections. In particular, after the pulse is emitted, the transducer may be used to measure the reflected acoustic pulses. Signals representative of the reflected acoustic pulses may be provided to a computational device for analysis. In particular, the reflections may be processed to calculate the blood flow velocities, as illustrated at 1110.

In an example, the blood flow through the blood vessel may be monitored based on the calculated velocities, as illustrated at 1112. In another example, a circulatory anomaly may be detected, as illustrated at 1114. For example, the circulatory anomaly may include restriction of the blood flow, such as by an embolism, a stenosis, or a vasospasm. Monitoring the blood flow through the blood vessel may include monitoring by comparing the blood flow velocity over time.

In an automated embodiment, the orientation of the piezoelectric transducer may be moved repeatedly to scan the interior volume of a patient's cranial cavity. For example, the transcranial probe may be adjusted using feedback from the analysis of the signals to orient the piezoelectric transducer so as to improve measurement of the velocity measurement for a particular vessel. In another example, the orientation of the piezoelectric transducer may be adjusted through broad ranges to locate blood vessels.

In a particular example, a control unit may include software to control transcranial Doppler signal transmission, positioning, and initial signal collection and processing. For example, the control unit may control characteristics of the probe, such as transmission depth, power levels, receiver gain, transmit burst length, receiver gate widths, and any combination thereof. The controller may perform signal demodulation and generate outputs, such as auditory or visual signals. In addition, the controller may provide data output to a computational device, such as a personal computer. The personal computer may permit manipulation of settings on the controller, display and manipulation of data, and storage of data.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A transcranial Doppler probe comprising:
   a spherical bearing;
   a mount including a piezoelectric transducer and pivotally attached to the spherical bearing;
   first and second motors;
   a first drive lever coupled to the first motor, the first drive level including a first drive arm having a first drive surface;
   a second drive lever coupled to the second motor and including a second drive arm having a second drive surface; and
   first and second rods coupled to the mount, the first rod in slidable contact with the first drive surface, the second rod in slidable contact with the second drive surface, the first rod configured to pivot the piezoelectric transducer around a first pivot axis and the second rod configured to pivot the piezoelectric transducer around a second pivot axis.

2. The transcranial Doppler probe of claim 1, wherein a pivot range around the first pivot axis is at least about 15.0° relative to a plane parallel to a horizontal plane of a housing of the transcranial Doppler probe.

3. The transcranial Doppler probe of claim 2, wherein the pivot range around the first pivot axis is at least about 20.0°.

4. The transcranial Doppler probe of claim 3, wherein the pivot range around the first pivot axis is at least about 30.0°.

5. The transcranial Doppler probe of claim 1, wherein a pivot range around the second pivot axis is at least about 15.0° relative to a plane parallel to a horizontal plane of a housing of the transcranial Doppler probe.

6. The transcranial Doppler probe of claim 5, wherein the pivot range around the second pivot axis is at least about 20.0°.

7. The transcranial Doppler probe of claim 6, wherein the pivot range around the second pivot axis is at least about 30.0°.

8. The transcranial Doppler probe of claim 1, wherein the transcranial Doppler probe is a wireless transcranial Doppler probe.

9. The transcranial Doppler probe of claim 1, wherein the first motor causes rotation around a first drive axis and the second motor causes rotation around a second drive axis, the first and second pivot axes askew from the first and second drive axes.

10. The transcranial Doppler probe of claim 9, wherein the first and second drive axes are parallel.

11. The transcranial Doppler probe of claim 1, wherein the first drive lever includes a first spring to motivate the first rod toward the first drive surface.

12. The transcranial Doppler probe of claim 11, wherein the second drive lever includes a second spring to motivate the second rod toward the second drive surface.

13. A transcranial Doppler probe comprising:
   a mount including a piezoelectric transducer;
   a first motor mechanically coupled to the mount via a first drive lever and a first rod slidably coupled to the first drive lever and coupled to the mount, the first motor configured to pivot the piezoelectric transducer around a first pivot axis; and
   a second motor mechanically coupled to the mount via a second drive lever and a second rod slidably coupled to the second drive lever and coupled to the mount, the second motor configured to pivot the piezoelectric transducer around a second pivot axis, the second pivot axis being perpendicular to the first pivot axis;
   wherein the first and second motors are arranged in parallel.

14. The transcranial Doppler probe of claim 13, wherein a pivot range around the first pivot axis is at least about 15.0° relative to a plane parallel to a horizontal plane of a housing of the transcranial Doppler probe.

15. The transcranial Doppler probe of claim 13, wherein a pivot range around the second pivot axis is at least about 15.0° relative to a plane parallel to a horizontal plane of a housing of the transcranial Doppler probe.

16. The transcranial Doppler probe of claim 13, wherein the first and second motors define respective first and second parallel drive axes, the first and second pivot axes being askew from the first and second drive axes.

17. The transcranial Doppler probe of claim 13, wherein the first drive lever includes a first arm having a first drive surface, the first rod in slidable contact with the first drive surface.

18. The transcranial Doppler probe of claim 17, wherein first drive lever includes a spring to motivate the first rod to the first drive surface.

19. The transcranial Doppler probe of claim 17, wherein the second drive lever includes a second arm having a second drive surface, the second rod in slidable contact with the second drive surface.

20. A transcranial Doppler probe comprising:
a spherical bearing;
a mount including a piezoelectric transducer and pivotally attached to the spherical bearing;
first and second rods coupled to the mount;
first and second drive levers;
a first motor coupled the first drive lever having a first drive surface slidably coupled to the first rod, the first motor configured to cause movement of the first rod to pivot the piezoelectric transducer around a first pivot axis; and
a second motor coupled to the second drive having a second drive surface slidably coupled to the second rod, the second motor configured to cause movement of the second rod to pivot the piezoelectric transducer around a second pivot axis,
wherein the first and second motors are arranged in parallel and second axis is perpendicular to the first axis.

* * * * *